US012800540B2

(12) United States Patent
De Wael et al.

(10) Patent No.: US 12,800,540 B2
(45) Date of Patent: Nov. 17, 2026

(54) PHOTO-ELECTROCHEMICAL PARTICLE ASSAY

(71) Applicant: UNIVERSITEIT ANTWERPEN, Antwerp (BE)

(72) Inventors: Karolien De Wael, Antwerp (BE); Saranya Thiruvottriyur Shanmugam, Antwerp (BE)

(73) Assignee: UNIVERSITEIT ANTWERPEN, Antwerp (BE)

(*) Notice: Subject to any disclaimer, the term of this patent is extended or adjusted under 35 U.S.C. 154(b) by 446 days.

(21) Appl. No.: 18/569,473

(22) PCT Filed: Jun. 30, 2022

(86) PCT No.: PCT/EP2022/068058
§ 371 (c)(1),
(2) Date: Dec. 12, 2023

(87) PCT Pub. No.: WO2023/275243
PCT Pub. Date: Jan. 5, 2023

(65) Prior Publication Data

US 2024/0219339 A1 Jul. 4, 2024

(30) Foreign Application Priority Data

Jun. 30, 2021 (EP) .................................... 21182783

(51) Int. Cl.

| | |
|---|---|
| ***G01N 27/327*** | (2006.01) |
| ***C12Q 1/6827*** | (2018.01) |
| ***C12Q 1/6837*** | (2018.01) |
| ***C12Q 1/6876*** | (2018.01) |
| ***G01N 27/413*** | (2006.01) |

(52) U.S. Cl.
CPC ....... *G01N 27/3276* (2013.01); *C12Q 1/6837* (2013.01); *C12Q 1/6876* (2013.01); *G01N 27/3277* (2013.01); *G01N 27/413* (2013.01); *C12Q 1/6827* (2013.01); *C12Q 2600/16* (2013.01); *C12Q 2600/178* (2013.01)

(58) Field of Classification Search
CPC ........... G01N 27/3276; G01N 27/3277; G01N 27/413; G01N 33/54326; G01N 33/5438; C12Q 1/6837; C12Q 1/6876; C12Q 1/6827; C12Q 2600/16; C12Q 2600/178; C12Q 1/6825; C12Q 2563/149; C12Q 2565/607
See application file for complete search history.

(56) References Cited

U.S. PATENT DOCUMENTS

2004/0175696 A1 9/2004 Ullman et al.
2019/0017955 A1 1/2019 De Wael et al.
2019/0048402 A1 2/2019 Pingarrón et al.

FOREIGN PATENT DOCUMENTS

WO 2017137192 A1 8/2017
WO 2019012114 A1 1/2019

OTHER PUBLICATIONS

International Search Report and Written Opinion dated Oct. 10, 2022 from International Patent Application PCT/EP2022/068058.

*Primary Examiner* — Brian J. Sines
(74) *Attorney, Agent, or Firm* — Amster, Rothstein & Ebenstein LLP

(57) ABSTRACT

This invention discloses a particular photo-electrochemical method for the quantification of biological components involving type II photosensitizers and particles to enhance the photo-electrochemical signal.

18 Claims, 8 Drawing Sheets

Specification includes a Sequence Listing.

SEQUENCE LISTING

<160> NUMBER OF SEQ ID NOS: 14

<210> SEQ ID NO 1
<211> LENGTH: 12
<212> TYPE: DNA
<213> ORGANISM: Artificial Sequence
<220> FEATURE:
<223> OTHER INFORMATION: Detection of miR-145

<400> SEQUENCE: 1
ggaaaactgg ac 12

<210> SEQ ID NO 2
<211> LENGTH: 11
<212> TYPE: DNA
<213> ORGANISM: Artificial Sequence
<220> FEATURE:
<223> OTHER INFORMATION: Capture miR-145

<400> SEQUENCE: 2
agggattcct g 11

<210> SEQ ID NO 3
<211> LENGTH: 23
<212> TYPE: RNA
<213> ORGANISM: Artificial Sequence
<220> FEATURE:
<223> OTHER INFORMATION: Target miR-145

<400> SEQUENCE: 3
guccaguuuu cccaggaauc ccu 23

<210> SEQ ID NO 4
<211> LENGTH: 11
<212> TYPE: DNA
<213> ORGANISM: Artificial Sequence
<220> FEATURE:
<223> OTHER INFORMATION: Detection of miR-141

<400> SEQUENCE: 4
agacagtgtt a 11

<210> SEQ ID NO 5
<211> LENGTH: 11
<212> TYPE: DNA
<213> ORGANISM: Artificial Sequence
<220> FEATURE:
<223> OTHER INFORMATION: Capture miR-141

<400> SEQUENCE: 5
ccatctttac c 11

<210> SEQ ID NO 6
<211> LENGTH: 22
<212> TYPE: RNA
<213> ORGANISM: Artificial Sequence
<220> FEATURE:
<223> OTHER INFORMATION: Target miR-141

<400> SEQUENCE: 6
uaacacuguc ugguaaagau gg 22

<210> SEQ ID NO 7
<211> LENGTH: 12
<212> TYPE: DNA
<213> ORGANISM: Artificial Sequence
<220> FEATURE:
<223> OTHER INFORMATION: Detection miR-375

<400> SEQUENCE: 7
cgaacgaaca aa 12

<210> SEQ ID NO 8
<211> LENGTH: 10
<212> TYPE: DNA
<213> ORGANISM: Artificial Sequence
<220> FEATURE:
<223> OTHER INFORMATION: Capture miR-375

<400> SEQUENCE: 8
tcacgcgagc 10

<210> SEQ ID NO 9
<211> LENGTH: 21
<212> TYPE: RNA
<213> ORGANISM: Artificial Sequence
<220> FEATURE:
<223> OTHER INFORMATION: Target miR-375

<400> SEQUENCE: 9
uuuguucguu cgcucgcgug a 21

<210> SEQ ID NO 10
<211> LENGTH: 18
<212> TYPE: DNA
<213> ORGANISM: Artificial Sequence
<220> FEATURE:
<223> OTHER INFORMATION: Detection sequence complementary to miR-21

<400> SEQUENCE: 10
tcaacatcag tctgataa 18

<210> SEQ ID NO 11
<211> LENGTH: 22
<212> TYPE: DNA
<213> ORGANISM: Artificial Sequence
<220> FEATURE:
<223> OTHER INFORMATION: Capture sequence complementary to miR-21

<400> SEQUENCE: 11
tagcttatca gactgatgtt ga 22

<210> SEQ ID NO 12
<211> LENGTH: 17
<212> TYPE: DNA
<213> ORGANISM: Artificial Sequence
<220> FEATURE:
<223> OTHER INFORMATION: Detection  sequence complementary to KRAS G12C

<400> SEQUENCE: 12
cgtcaaggca ctcttgc 17

<210> SEQ ID NO 13
<211> LENGTH: 17
<212> TYPE: DNA
<213> ORGANISM: Artificial Sequence
<220> FEATURE:
<223> OTHER INFORMATION: Capture sequence complementary to KRAS G12C

<400> SEQUENCE: 13
ctacgccaca agctcca 17

-continued

```
<210> SEQ ID NO 14
<211> LENGTH: 34
<212> TYPE: DNA
<213> ORGANISM: Artificial Sequence
<220> FEATURE:
<223> OTHER INFORMATION: Target sequence KRASG12C

<400> SEQUENCE: 14

tggagcttgt ggcgtaggca agagtgcctt gacg                          34
```

PHOTO-ELECTROCHEMICAL PARTICLE ASSAY

CROSS-REFERENCE TO RELATED APPLICATIONS

This application is a U.S. national stage entry under 35 U.S.C. § 371 of PCT International Patent Application No. PCT/EP2022/068058, filed Jun. 30, 2022, which claims priority to European Patent Application No. 21182783.7, filed Jun. 30, 2021, the contents of each of which are incorporated herein by reference in their entirety.

FIELD OF THE INVENTION

The present invention is situated in the field of the detection and/or quantification of biological components using photo-electrochemistry. The present invention is further related to the specific use of type II photosensitizers in combination with particles to enhance the photo-electrochemical effect.

BACKGROUND OF THE INVENTION

The photo-electrochemical detection and quantification of biological components is based on the combination of aerobic photo-catalysis and electrochemical analysis. The photo-electrochemical detection of biological components has been described based on the use of type II photosensitizers which under light illumination generates a reactive singlet oxygen ($^1O_2$), as well as reactive oxygen species (ROS). In the presence of a redox reporter, a current is generated, and this photocurrent can then be measured electrochemically. A particular advantage of this method is the fact that an electrochemical signal is generated by switching the light illumination on and/or off. Hereby, a clear distinction can be made between the background signal and the photocurrent.

The concept of photo-electrochemical detection of biological components has been used already in Trashin et al. (2017) for the detection of oligonucleotides. More specifically, Trashin et al. used pheorphorbide a, a chlorophyll-derived component as photosensitizer in combination with hydroquinone as redox reporter to detect microRNA (miR), in particular miR-21, an important biomarker for cancer diagnosis or cardiovascular diseases diagnosis. In this set-up, the photosensitizer was labeled to an oligonucleotide sequence of 15 base pairs whereas the electrode was modified with a complementary DNA probe. Negative controls were executed with non-complementary DNA probes of the same length. Although a clear difference in photocurrent signal was established between the experiments involving complementary electrodes versus experiments with non-complementary electrodes, the established sensitivity was too low to be used as a diagnostic method, especially in a clinical setting.

Hence, there is a clear need for methods which enhance the photo-electrochemical signal to obtain lower detection limits for biological components. Sensitive and specific detection methodologies are of great interest to be used in the field of diagnostics (including infectious diseases), healthcare monitoring, industrial process control, environmental control, . . . .

SUMMARY OF THE INVENTION

This invention discloses an improved method for the detection and/or quantification of biological components in a sample. The present invention enhances the photo-electrochemical signal in the detection and/or quantification of biological components resulting in a more sensitive and reliable assay. More particularly, the inventors have elaborated a photo-electrochemical method for the detection and/or quantification of at least one biological component. This detection and/or quantification is achieved by contacting a complex that is formed specifically by (indirectly) binding said biological component to a particle and a type II photosensitizer with an electrode but keeping μm distance therefrom. The aforementioned complex comprises of a first binding agent labeled with a type II photosensitizer capable of binding to the biological component of interest and a second binding agent capable of binding to the biological component of interest or to the first binding agent without interfering with the binding of the first binding agent to the biological component, whereby the second binding agent is linked to a particle. The complex is formed only in the presence of said biological component and thus will only be formed when said reagents are contacted with said biological component. The binding between the two binding agents with the biological component is specific such that the generated photocurrent correlates with the concentration of the biological component present in a given sample. The said complex is illuminated in the presence of a redox reporter thereby allowing detection of the generated photocurrent generated by the oxidation of the redox reporter. As an advantage, the new method results in improved detection limits, relevant for clinical applications. As a secondary advantage, the new method allows the introduction of multiplex assays by introducing different type II photosensitizers on different first binding agents.

In particular embodiments, the aforementioned complex comprises of a first binding agent labeled with a type II photosensitizer capable of binding to the biological component of interest and a second binding agent capable of binding to the biological component of interest or to the first binding agent without interfering with the binding of the first binding agent to the biological component, whereby the second binding agent is linked to a particle. The complex is formed only in the presence of said biological component and thus will only be formed when said reagents are contacted with said biological component. The binding between the two binding agents with the biological component is specific such that the generated photocurrent correlates with the concentration of the biological component present in a given sample. As an advantage, the new methodology results in improved detection limits, relevant for clinical applications. As a secondary advantage, the new methodology allows the introduction of multiplex assays by introducing different type II photosensitizers on different first binding agents.

In particular embodiments, the invention thus provides a photo-electrochemical method for the detection and/or quantification of at least one biological component involving (a) contacting a complex with an electrode, said complex comprising (i) a first binding agent labeled with a type II photosensitizer and (ii) a second binding agent linked to a particle; and wherein at least one of said first or second binding agent is capable of binding to said biological component and if one of said first or second binding agent is not capable of binding to said biological component, said binding agent is capable of binding to said other binding agent, whereby the binding of one or more of said binding agents to said biological component or to the other binding agent do not interfere with each other, more particularly the binding of said first and/or second binding agents to said biological component does not interfere with the binding of said first and/or second binding agents to said biological component and/or with the binding of said first and second binding agents to each other; The complex is further characterized in that said binding of said first binding agent to said biological component and/or said binding of said second binding agent to said first binding agent or to said biological component is specific such that a complex is formed only with said biological component; (b) illuminating said complex in the presence of a redox reporter and (c) detecting the photocurrent generated by the oxidation of said redox reporter at the surface of said electrode.

In particular embodiments the particles are magnetic particles and a magnetic field is used to contact the complex with the electrodes.

In particular embodiments, the complex is obtained by contacting a fluid sample with the biological component with a first binding agent labeled with a type II photosensitizer capable of binding to this biological component and a second binding agent capable of binding to the biological component or to the first binding agent without interfering with the binding of the first binding agent to the biological component, and where the second binding agent is linked to a particle.

In particular embodiments, the method is applied to quantify two or more biological components by contacting two or more complexes with an electrode, each complex having a different type II photosensitizer (sensitive to different excitation wavelengths) and the subsequent illumination at the different wavelengths and the individual detection of the different photocurrent signals, generated at the different individual wavelengths.

In particular embodiments, the method is used for the detection and/or quantification of RNA or DNA molecules and at least one of the first and second binding agents are capable of hybridizing with the RNA or DNA molecule of interest.

In particular embodiments, the method is used for the detection and/or quantification of protein sequences and at least one of the first and second binding agents are capable of binding with the protein sequences of interest.

In particular embodiments, the redox reporter is selected from the list of hydroquinone, 4-aminophenol, 2 chlorophenol, bisphenol A or a 1:1 mixture of hydroquinone:L-ascorbic acid.

In particular embodiments, the type II photosensitizer is selected from the list of chlorin e6, pheoporbide a, methyl pheophorbide, methylene blue, erythrosine, eosin, rosebengal.

In particular embodiments of the methods of the invention, the first binding agent is labeled with two or more type II photosensitizers.

In particular embodiments of the methods of the invention said complex further comprises one or more additional binding agents labeled with a type II photosensitizer, wherein said one or more additional binding agents are capable of binding to said first or second binding agents and/or to each other, wherein said binding of said additional binding agents to said first or second binding or to each other does not interfere with the binding of said first and second binding agents to the biological component or to each other.

A further related aspect of this invention is the photoelectrochemical system as a platform to execute the aforementioned method, involving an electrode, a first binding agent labeled with a type II photosensitizer capable of binding to the biological component of interest, a second binding agent capable of binding to the biological component of interest or to the first binding agent without interfering with the binding of the first binding agent to the biological component, and where the second binding agent is linked to a particle, and a redox reporter selected from the list of hydroquinone, 4-aminophenol, 2 chlorophenol, bisphenol A or a 1:1 mixture of hydroquinone:L-ascorbic acid.

A further related aspect of this invention is a diagnostic kit involving a first binding agent labeled with a type II photosensitizer capable of binding to the biological component of interest, a second binding agent capable of binding to the biological component of interest or to the first binding agent without interfering with the binding of the first binding agent to the biological component, and where the second binding agent is linked to a particle, and a redox reporter selected from the list of hydroquinone, 4-aminophenol, 2 chlorophenol, bisphenol A or a 1:1 mixture of hydroquinone:L-ascorbic acid.

In particular embodiments of the system or kit of the invention, the first binding agent is labeled with two or more type II photosensitizers.

In particular embodiments the system or kit of the invention further comprise one or more additional binding agents labeled with a type II photosensitizer, wherein said one or more additional binding agents are capable of binding to said first or second binding agents and/or to each other, wherein said binding of said additional binding agents to said first or second binding or to each other does not interfere with the binding of said first and second binding agents to the biological component or to each other.

DETAILED DESCRIPTION OF THE INVENTION

Figure 1:
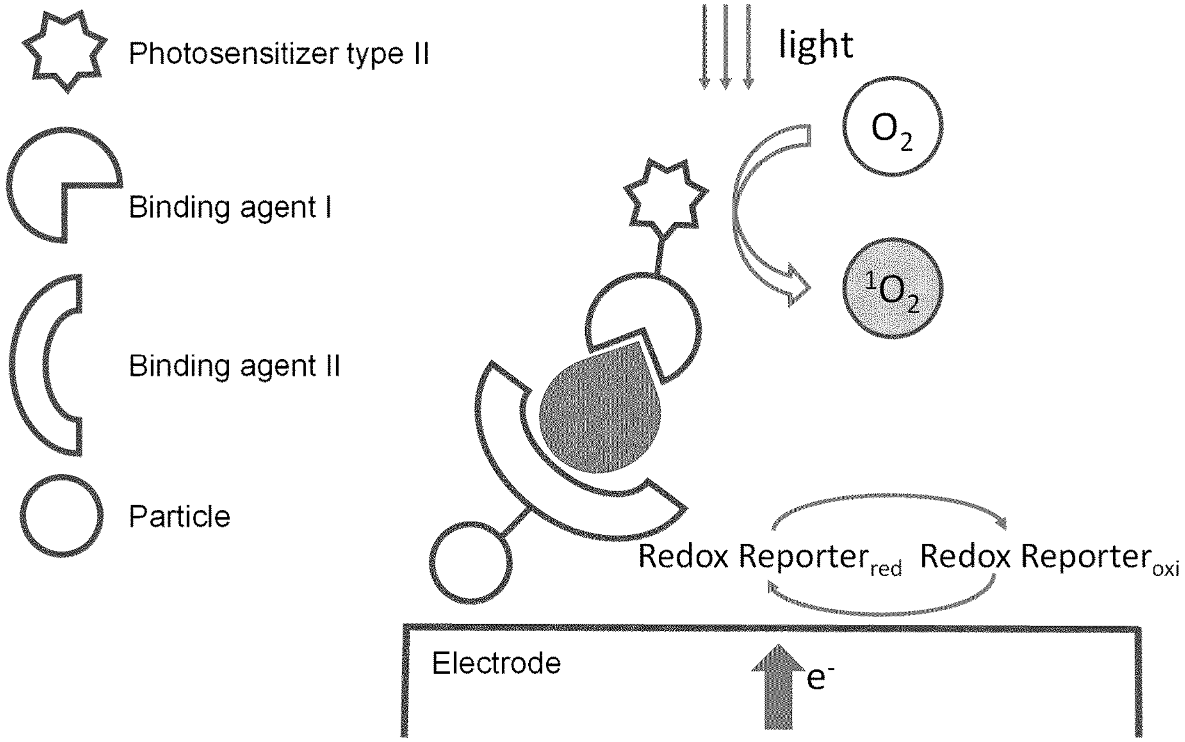
FIG. 1 represents a schematic view of the photo-electrochemical detection method.

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. It is to be understood that other embodiments may be utilised and structural or logical changes may be made without departing from the scope of the present invention. The following detailed description, therefore, is not to be taken in a limiting sense, and the scope of the present invention is defined by the appended claims.

The detailed description of the proposed method for the detection of biological components involves the specific use of type II photosensitizers in combination with particles to enhance the photo-electrochemical effect. By specific illumination of the present photosensitizer components, singlet oxygen is generated, as well as reactive oxygen species (ROS). The singlet oxygen and the associated ROS may oxidize specific redox reporter-components and the latter components may then be electrochemically reduced at electrodes to generate the reduced form of the redox reporter. The present inventors have identified a method of increasing the sensitivity of said assay by ensuring that the electrocatalytic redox cycle is generated at μm distance from the electrode surface by concentrating the complex closer to the surface of the electrode using particles. More particularly, the method involves ensuring that the label is contacted with the electrode via a particle. As will be evidenced by the Figures and the Examples, this method allows the detection of very low concentrations of biological components. Hence, this method can be used as diagnostic tool in different settings.

The means by which the biological component is captured in the methods of the present invention are not critical and will be determined based on the nature of the biological component. Typically, the methods comprise a binding agent that is coupled to the type II photosensitizer and a binding agent that is coupled to the particle. It will be understood by the skilled person that specificity of the method is ensured by the fact that none of the binding agents used bind to other biological components that could interfere with the specific detection of the biological component of interest. Accordingly, in preferred embodiments, the methods involve at least two binding agents, one of which is coupled to the type II photosensitizer label (hereinafter referred to as the first binding agent), and the other (hereinafter referred to as the second binding agent) is coupled to a particle. In order for the assay to be specific for said biological component, the means typically involve at least one binding agent capable of specifically binding to the biological component. It will be understood by the skilled person that the reference to "first" and "second" binding agent (or binding agent 1 and binding agent 2) herein is arbitrary and merely for practical purposes but does not imply a specific sequence of the method steps.

In particular embodiments, both the first and second binding agent are capable of binding to the biological component, and the binding of each of these binding agents to the biological component does not interfere with the binding of any of the other binding agents to the biological component. In particular embodiments, the first and second binding agent can be linked thereby effectively forming one binding agent with two binding sites capable of binding to said biological component. As noted above, to ensure specificity of the assay, at least one of the first and second binding agents is capable of specifically binding to the biological component. In particular embodiments, both of the first and second binding agents are capable of specifically binding to the biological component. Examples thereof are provided herein below.

In alternative embodiments, the first binding agent is capable of binding to the biological component and the second binding agent is capable of binding to said first binding agent which is capable of binding to said biological component. In these embodiments, the binding of said first binding agent to the biological component does not interfere with the binding of said second binding agent to said first binding agent. In alternative embodiments, the second binding agent is capable of binding to the biological component and the first binding agent is capable of binding to the second binding agent which can bind to the biological component. Similarly, in these embodiments, the binding of said second binding agent to the biological component does not interfere with the binding of said first binding agent to second first binding agent. To ensure specificity of the assay in these embodiments the binding to either the biological component or the binding agent should be specific. In particular embodiments, the binding agent capable of binding to the biological component is capable of specifically binding to the biological components. In these embodiments, the binding agent not capable of binding to the biological component may be capable of specifically binding to the binding agent which does bind the biological component in order to further improve specificity. Examples thereof are provided herein below.

It will be understood that it can be envisaged that the binding of the binding agents to the biological component and/or to another binding agent can be directly or indirectly. Indeed, it can be envisaged that a further "intermediate" binding agent is used to ensure binding to the biological molecule and said first or second binding agent bind to said biological molecule by way of said intermediate binding agent. In preferred embodiments however, the binding of said binding agent to said biological component is a direct binding. Examples of binding agents capable of directly binding to biological components are provided below. In preferred embodiments, where the first or second binding agent bind the other binding agent, the binding is (also) preferably but not necessarily a direct binding. Examples of binding agents capable of directly binding to other binding agents are provided below. Again, as indicated above, the methods of the invention envisage that the binding agents do not bind other biological components that could interfere with the specific detection of the biological component. Thus, as indicated herein, the binding agent that does not bind to the biological component of interest, binds to another binding agent but also does not bind to another biological component, as this would compromise the specific detection of the biological component of interest.

The methods of the present invention involve contacting a sample which may comprise the biological component of interest with the reagents described above. It is noted that in particular embodiments, the biological sample is contacted in a first step only with (one of) the binding agent(s) capable of binding to the biological component. After this step it may be possible to isolate the biological component bound to said binding agent from the sample. For instance, this may be the case where the binding agent capable of binding to said biological component is bound or can be bound to a solid surface, the methods may involve washing said surface to remove other components than the biological component bound to the binding agent.

In the methods of the present invention, the first binding agent is linked to a type II photosensitizer. The term "linked" as used herein refers to as coupled to the type II photosensitizer by a conjugating molecule between the first binding agent and the type II photosensitizer in such a way that this coupling is stable during the different steps of the photo-electrochemical method. In particular embodiments, the binding agent is a polynucleotide or a (poly)peptide. Methods of labeling nucleic acid or (poly)peptide sequences are known in the art and include enzymatic and chemical methods. In particular embodiments, where the binding agent is or comprises a nucleotide or amino acid sequence, the label can be present N- or C-terminally or at any other position in said sequence, provided that the label does not interfere with the binding of said binding agent to said biological component or to another binding agent. In particular embodiments, the first binding agent contains more than one type II photosensitizer molecule, such as two, three, four or more type II photosensitizer molecules. In the methods of the present invention, the second binding agent is linked to a particle. The term "linked" as used herein refers to a connection between the binding agent and the particle, which is stable during the different steps of the photo-electrochemical method. This can be a reversible or an irreversible connection. For instance this can be a chemical conjugation between the binding agent and the particle. Alternatively, the second binding agent may also be linked to a particle by means of a biomolecular interaction such as a streptavidin-biotin interaction. For instance, the particle can be linked to streptavidin and the second binding agent can have a biotin group in order to generate a second binding agent linked to a particle. In particular embodiments, the second binding agent is capable of binding to the biological component and the methods of the invention may involve contacting the sample with the second binding agent and thereafter separating the second binding agent linked to the particle from the sample based on the properties of said particle. The nature of the particle is discussed more in detail below but in particular embodiments the second binding agent is separated from said sample by way of a gravitational, magnetic or other force applied to said particle.

In the methods of the present invention, when contacting a sample which may comprise a biological component with the reagents described above, and if the biological component is present in the sample, the binding agent capable of binding to said biological component will bind thereto and a complex is formed comprising the biological component, the first binding agent linked to the type II photosensitizer and the second binding agent linked to the particle. In the methods of the invention, this complex is contacted with an electrode, whereby upon illumination of the complex, the distance between the type II photosensitizer and the electrode ensures the generation of singlet oxygen and reactive oxygen species (ROS) leading to the generation of the reduced form of the redox reporter, which can be detected.

In a particular embodiment the biological assay by means of the photo-electrochemical method is a sandwich assay with the use of two binding agents that are capable to bind independently with the biological component. The first binding agent is labeled with a type II photosensitizer whereas the second binding agent is labeled with a particle. The first and second binding agents are selected in such a way that there is no interference of the binding of binding agent 2 with the biological component bound to binding agent 1. The binding of the two binding agents is specific in such a way that a complex is formed only in the presence of the biological component, wherein the complex is composed of the biological component, the first binding agent labeled with a photosensitizer and the second binding agent labeled with a particle. A schematic overview of the elaborated biological assay is illustrated in FIG. 1.

The biological components that can be detected may include nucleic acid sequences such as DNA- or RNA-sequences, including cell-free nucleic acid sequences such as miRNA or tumor circulating DNA (ctDNA). These DNA- or RNA-sequences may also originate from other biological organisms, such as but not limited to viruses, bacteria, fungi or parasites. Hence, the assay can also serve as a methodology for the fast diagnosis of infectious diseases. In a particular embodiment, the DNA- or RNA-sequences have a basepair (bp) composition of less than 100 bp, more particularly less than 50 bp and preferably at least 15 bp.

Other biological components that can be detected may include proteins sequences (such as peptides, oligopeptides, polypeptides), macromolecular assemblies (viruses, phages, . . . ), cellular components (organelles such as exosomes, ribosomes, . . . ), cells, . . . .

The binding agents that can be used for the detection of the biological components include any structures that can ensure binding with another molecule as described herein and may include complementary RNA/DNA sequences, peptide aptamers, oligonucleotide aptamers, peptide nucleic acids, locked nucleic acids, antibodies or binding fragments thereof, nanobodies, alphabodies, affimers, molecular imprinted polymers (MIP), DNAzymes, receptors, . . . . Accordingly, it will be understood that in the context of the present invention the reference of a binding agent "capable of binding to" a biological component encompasses all biomolecular interactions, based on covalent interactions or non-covalent interactions (such as electrostatic interactions, Van der Waal interactions, dispersion interaction, hydrogen bonds, hydrophobic interaction, . . . ). Specifically, this involves the typical hybridization interactions for RNA/DNA sequences, the typical protein/protein interactions (e.g. antigen/antibody interactions, antigen/nanobody interactions, antigen/alphabody interactions, . . . ), . . . .

It will be understood that in the context of the present invention a binding agent capable of "specifically binding" to a biological component of interest typically refers to the fact that it will bind only the (one or more) biological component(s) of interest (and will have typically been manufactured so as to bind only the biological component(s) of interest). In particular embodiments "specific binding" will refer to the ability to distinguish between the biological component(s) of interest and other components potentially present in the sample, such that absolute specificity is not required. The same concept applies to the binding agent capable of specifically binding to another binding agent. The skilled person will be familiar with the conditions and criteria of "specific binding" for the different types of binding agents envisaged herein. More particularly in the context of nucleotide hybridization and antigen/antibody binding, but also for other known binding agents, such concepts are well-established.

In particular embodiments, the biological component is DNA and RNA and the binding agent capable of binding to a biological component which is a DNA or RNA oligonucleotide is a complementary oligonucleotide or probe. In particular embodiments, where the biological component is a DNA or RNA oligonucleotide both the first and second binding agent are DNA or RNA probes with complementarity to different regions of the biological component such that the binding of these first and second binding agents to the biological component does not interfere with each other. In particular embodiments only one of the first and second binding agent binds specifically to said biological component and the other binding agent is a DNA or RNA probe which binds non-specifically to said biological agent. In preferred embodiments however both the first and second binding agents bind specifically to the biological component. In particular embodiments, the biological component is a DNA or RNA oligonucleotide and only one of the first and second binding agents are capable of hybridizing to the biological component. In these embodiments the other binding agent is capable of hybridizing to the binding agent which does bind the biological component. For instance, the first binding agent binds to the biological component and the second binding agent is capable of binding to the first binding agent. As detailed above it is important that the binding of the binding agent(s) to the biological molecule and/or the binding of one binding agent to another binding agent do not interfere with each other. Where the binding agent is a DNA probe this can be ensured by probes which hybridize to different regions of the biological agent or the binding agent. More particularly, a first binding agent can be used which is a probe which contains a first region capable of hybridizing to the DNA/RNA molecule of interest and a second region capable of hybridizing to a probe linked to a particle (which is the second binding agent). More particularly, this hybridization step can be executed at specific temperatures in order to obtain optimal binding efficiency and specificity between the DNA/RNA molecule of interest and at least any of the two binding agents.

In particular embodiments, the biological component is a peptide (or another molecule capable of eliciting an antibody response) and the binding agent capable of binding to a biological component is a protein binding agent such as an antibody, receptor, or a helix-based binding agent. In particular embodiments, where the biological component is a peptide molecule both the first and second binding agent are antibodies with ability to bind to different regions of the biological component such that the binding of these first and second binding agents to the biological component does not interfere. In particular embodiments only one of the first and second binding agent binds specifically to said biological component and the other binding agent is a protein-based reagent which binds non-specifically to said biological agent. In preferred embodiments however both the first and second binding agents bind specifically to the biological component. In particular embodiments, the biological component is a peptide molecule and only one of the first and second binding agent is capable of binding to the biological component. In these embodiments the other binding agent is capable of binding to the binding agent which does bind the biological component. For instance, the first binding agent is an antibody that binds to the biological component and the second binding agent is an antibody capable of binding to the constant region of the first binding agent. As detailed above it is important to note that the binding of the binding agent(s) to the biological molecule and/or the binding of one binding agent to another binding agent do not interfere with each other. Where both binding agents are nanobodies, this can be ensured by two different nanobodies which hybridize to different regions of the biological component. Where one binding agent is an antibody and the other binding agent is an aptamer, specifically selected to bind to this antibody but not to the biological component, this can be ensured in a first step by the binding of the antibody with the biological component and in a second step by the binding of this structure with the aptamer.

The photosensitizer used in the present invention must originate from the class of type II photosensitizers, producing singlet oxygen, as the presence of singlet oxygen is needed to oxidize the redox reporter, and hence to start the oxidation-reduction process at the surface of the electrode. Possible type II photosensitizer molecules may include following components (and their derivatives): chlorin e6, pheophorbide a, methyl pheophorbide, methylene blue, erythrosine, eosin, rosebengal, acridine, phenalenone, cercosporin, hypocrelin, phloxine B, chlorophyll, riboflavin, flavin nucleotide, (pseudo)hypericin, porphyrins, phthalocyanines, BODIPY-based molecules . . . .

The methods of the invention make use of a binding agent linked to a particle. The particle is preferably in the range of 0.1-10 μm, more particularly in the range of 1-10 μm, more particularly in the range of 1-5 μm, preferably 2.5 to 3 μm, such as about 2.7 μm.

The nature of the particles can be influenced by the way that the particles are to be contacted with the electrode. The contacting of the particles to the electrodes in the methods of the invention is such that it allows the particles to interact with the surface of the electrode and preferably concentrate at the surface of the electrode. This can involve a force, such as a magnetic or electronic force, a gravitational force, such as sedimentation or centrifugation.

In particular embodiments, the particles are magnetic particles. The use of magnetic particles has as particular benefit that (i) magnetic attraction can be used to separate/isolate the biological component from the remainder of the sample, (ii) magnetic attraction can be used to contact the complex more closely to the electrode and/or (iii) to concentrate the complex close to the working electrode surface. Although magnetic particles are used as a preferred embodiment, the use of other (non-magnetic) particles is also possible. Examples of non-magnetic particles include particles composed of silica, polystyrene, polymeric microparticles or hybrid particles composed of multiple materials. Where the second binding agent is linked to a non-magnetic particle, the separation/isolation of the biological component using said particle can be achieved by applying a gravitational force (e.g. sedimentation or centrifugation). In these embodiments, the contacting of the complex with the electrode can also be achieved by applying a gravitational force (e.g. sedimentation or centrifugation). The amount of beads introduced on the electrodes for the execution of a single assay may be preferably in the range of 1 μg-10000 μg, more particularly in the range of 10 μg-1000 μg, preferably 100 μg.

In particular embodiments, the complex that is brought into contact with the electrode during the photo-electrochemical method includes the biological component, a first binding agent labeled with a type II photosensitizer, and a second binding agent labeled with a particle. The first and second binding agents are selected in such a way that there is no interference of the binding of binding agent 2 with the biological component bound to binding agent 1. The binding of the two binding agents is specific in such a way that a complex is formed composed of the biological component, the first binding agent labeled with a photosensitizer and the second binding agent labeled with a particle. The sequence of the binding of the different binding agents with the biological component is exchangeable as long as both binding agents are linked in a specific way in order to obtain a quantitative analysis of the biological component.

The obtained complex can be the result of any type of assay, including but not limited to direct or indirect binding assays, competition assays, sandwich assays, based on the molecular interaction used, such as DNA/RNA hybridization, protein-protein interactions etc described above. For instance assays can take the typical configuration of immunoassays such as competitive homogeneous immunoassays, competitive heterogeneous immunoassays, one-site noncompetitive immunoassays, two-site noncompetitive immunoassays, . . . .

The methods of the present invention comprise contacting the complex formed when contacting the biological component with the binding agents with an electrode as indicated above. To achieve an optimal signal, it is preferred that the complex is located at 0.1-10 μm distance, more particularly 1-10 μm distance, more particularly 1-5 μm, preferably 2-3 μm distance from the electrodes. In particular embodiments, this distance is ensured by the size of the particle and the attraction of the particle to the surface of the electrode. Additionally or alternatively other components can (help) ensure this distance between the photosensitizer and the electrode. Examples of suitable components include for instance DNA origami nanostructures or protein complexes.

The methods of the present invention further comprise illuminating the complex in the presence of a redox reporter. The redox reporter components in the photo-electrochemical method is not critical and can be selected by the skilled person. For instance, the redox reporter can be selected from the list of hydroquinone, catechol, phenol, bisphenol-A, 3-nitrophenol, 4-nitrophenol, 2-aminophenol, 3-aminophenol, 4-aminophenol, 2-amino-4-chlorophenol, 3 cyanophenol, 4-cyanophenol, amoxicillin, 1.1'-ferrocene-dimethanol 2 chlorophenol, L-ascorbic acid, or can be introduced as a mixtures thereof such as for example a 1:1 mixture of hydroquinone:L-ascorbic acid or a 1:10 mixture of hydroquinone:L-ascorbic acid or a 1:100 mixture of hydroquinone:L-ascorbic acid. The concentration range of the redox reporter may be preferably in the range between 0.01 mM-100 mM, more preferably between 0.1 mM-10 mM, and is preferably 1 mM.

The methods of the present invention further comprise detecting the photocurrent generated by the oxidation of said redox reporter at the surface of said electrode. The photocurrent is generated upon illumination at an appropriate wavelength that is compatible with the type II photosensitizer. The illumination of the complex can be achieved by a wide variety of selective light sources, including but not limited to lasers, LED, white light with monochromators, . . . . The illumination can take place continuously or in a pulsed way. The photocurrent that is generated at the surface of the electrode can be measured amperometrically or by voltammetric techniques by a wide variety of electrode surfaces, including but not limited to gold thin film or thick film sputtered electrodes, gold (screen printed) electrodes, carbon (screen printed) electrodes, carbon nanotubes (screen printed) electrodes, graphene oxide-carbon (printed) electrodes, mesoporous carbon (printed) electrodes, carbon nanofiber (printed) electrodes, cobalt(II)phthalocyanine carbon (printed) electrodes, polyaniline screen printed electrodes, . . . . In an amperometric setup, the photocurrents can be measured in a potential range preferably between +0.05V and −0.6V, more preferably between −0.1V and −0.4V, and is preferably −0.2V.

In particular embodiments, the methods involve detecting two or more biological components in a sample. Hereto, two or more complexes, labeled with two or more different type II photosensitizers that are sensitive to a different wavelength, are contacted to the surface of an electrode and illuminated with the respective wavelengths. The different photocurrents (at the corresponding wavelengths) are representative for the presence of the different biological components. In particular embodiments, both the first and the second binding agent are specific for each of the biological components of interest. In alternative embodiments, the second binding agent is identical for the two or more biological components, whereas the first binding agent labeled with the different type II photosensitizers is specific for the two or more biological components. In particular embodiments, the second binding agent is specific for each of the two or more biological components and the first binding agent labeled with the type II photosensitizer is specific for the two or more specific second binding agents. Examples of suitable combinations of type II photosensitizers include but are not limited to methylene blue (suitable for measurements using the red LED) and erythrosine or eosin (both suitable measurements using the green LED), . . . .

In particular embodiments, the methods of the invention may comprise the use of more than one binding agent linked to a type II photosensitizer, to further amplify the signal. In these embodiments, the additional labeled binding agents can form part of the complex by binding either to one of the other elements of the complex, i.e. the biological component or the first or second binding agent. It will be understood to the skilled person that this binding of the additional binding agents should not interfere with the formation of the complex between the first and second binding agent and the biological component as described herein. In particular embodiments, more than one additional binding agent linked to a photosensitizer is used, wherein only one of the additional binding agents bind to one of the components of the complex and the remainder of the labeled binding agents are capable of binding to each other. For instance, in the methods of the invention, the complex can comprise a third binding agent linked to a photosensitizer which is capable of binding to the first binding agent. Optionally, a fourth binding agent linked to a photosensitizer can form part of the complex by binding to the third binding agent, etc. For instance, where the binding agents are polynucleotide sequences, two additional sequences can be used as binding agents which bind to each other with an overhang N- and C-terminally such that they can form a chain. This principle is also referred to as "hybridization chain reaction", and, given that each of these polynucleotide sequences are labelled, this can lead to a significant amplification of the signal which lower the detection limit of the methods of the invention.

Another aspect of the invention relates to a photo-electrochemical system involving an electrode, the first binding agent labeled with a type II photosensitizer capable of binding to said biological component, a second binding agent capable of binding to said biological component or to said first binding agent without interfering with the binding of said first binding agent to said biological component, said second binding agent being linked to a particle wherein said binding of said first binding agent to said biological component and/or said binding of said second binding agent to said first binding agent or to said biological component is specific such that a complex is formed only with said biological component, and a redox reporter. In the systems of the invention the first binding agent and second binding agent are as described herein above for the methods of the invention.

Another aspect of the invention relates to a kit for the execution of the photo-electrochemical method involving, the first binding agent labeled with a type II photosensitizer capable of binding to said biological component, a second binding agent capable of binding to said biological component or to said first binding agent without interfering with the binding of said first binding agent to said biological component, said second binding agent being linked to a particle wherein said binding of said first binding agent to said biological component and/or said binding of said second binding agent to said first binding agent or to said biological component is specific such that a complex is formed only with said biological component, and a redox reporter. In the kits of the invention the first binding agent and second binding agent are as described herein above for the methods of the invention.

As detailed herein for the methods of the invention, it is also envisaged that the in particular embodiments of the system or kit of the invention the first binding agent is labeled with two or more type II photosensitizers.

As also detailed herein for the methods of the invention, is is envisaged that in particular embodiments the system or kit of the invention may further comprise one or more additional binding agents labeled with a type II photosensitizer, wherein said one or more additional binding agents are capable of binding to said first or second binding agents and/or to each other, wherein said binding of said additional binding agents to said first or second binding or to each other does not interfere with the binding of said first and second binding agents to the biological component or to each other.

EXAMPLES

Chlorin e 6 (ChlE6, purity≥98%, Cayman chemical company, USA), methylene blue (MetB, Reag. Ph Eur, Merck KgaA, Germany), erythrosine (Ery, purity≥95%, Merck Schuchardt OHG), hydroquinone (HQ, Acros Organics, Belgium) were used as received.

DNA probes modified at 5' or 3' end by the chromophores were synthesized and purified by Eurogentec (Belgium),) except modification with MetB which was prepared by Metabion (Germany). The chromophores were attached to the DNA via a amino-C6 linker using either activated carboxylic or isothiocyanate functionality. DNA were modified at 5'-end by thiol C6 ($HS—(CH_2)_6—$) or Biotin-TEG (a 16-atom spacer based on a triethylene glycol) by Eurogentec (Belgium) for immobilization on gold and streptavidin-modified surfaces, respectively. The detailed list of all the sequences used in are listed in the below table;

| Name | 5' modification | Sequence (5'→3') | 3' modification |
|---|---|---|---|
| Sequences used for detection of miR-145 (Sandwich hybrid assay) | | | |
| Detection | | GGAAAACTGGAC (SEQ ID NO: 1) | ChlE6 |
| Capture | Biotin-TEG | AGGGATTCCTG (SEQ ID NO: 2) | |
| Target | | GUCCAGUUUUCCCAGGAAUCCCU (SEQ ID NO: 3) | |
| Sequences used for detection of miR-141 (Sandwich hybrid assay) | | | |
| Detection | | AGACAGTGTTA (SEQ ID NO: 4) | ChlE6 |
| Capture | Biotin-TEG | CCATCTTTACC (SEQ ID NO: 5) | |
| Target | | UAACACUGUCUGGUAAAGAUGG (SEQ ID NO: 6) | |
| Sequences used for detection of miR-375 (Sandwich hybrid assay) | | | |
| Detection | | CGAACGAACAAA (SEQ ID NO: 7) | ChlE6 |
| Capture | Biotin-TEG | TCACGCGAGC (SEQ ID NO: 8) | |
| Target | | UUUGUUCGUUC-GCUCGCGUG-A (SEQ ID NO: 9) | |
| Sequences used for detection of two-strand hybridization with detection sequence complementary to miR-21 (duplex assay) | | | |
| Detection | MetB/Chle6/Ery | TCAACATCAGTCTGATAA (SEQ ID NO: 10) | |
| Capture | Biotin-TEG/ HS-$(CH_2)_6$ | TAGCTTATCAGACTGATGTTGA (SEQ ID NO: 11) | |
| Sequences used for detection of miR-145 with signal amplification (Sandwich hybrid assay) | | | |
| Detection 1 PS | MetB | GGAAAACTGGAC (SEQ ID NO: 1) | |
| Detection 3 PS | MetB | GGAAAA(MetB-dT)CTGGAC (SEQ ID NO: 1) | MetB |
| Capture | Biotin-TEG | AGGGATTCCTG (SEQ ID NO: 2) | |
| Target | | GUCCAGUUUUCCCAGGAAUCCCU (SEQ ID NO: 3) | |
| Sequences used for detection of KRAS G12C (Sandwich hybrid assay) | | | |
| Detection | | CGTCAAGGCACTCTTGC (SEQ ID NO: 12) | ChlE6 |
| Capture | Biotin-TEG | CTACGCCACAAGCTCCA (SEQ ID NO: 13) | |
| Target | | TGGAGCTTGTGGCGTAGGCAAGAGTGCCTTG ACG (SEQ ID NO: 14) | |

Streptavidin-coated magnetic beads (M280-Dynabeads, Invitrogen) were used for the assay with magnetic beads. A 2×TE buffer solution (pH 7.5), containing 10 mM Tris, 1 mM EDTA (Titriplex III), and 2 M NaCl was prepared and used for the assay. The pH of the buffer was adjusted using HCl. This 2×TE-buffer was mixed with (i) Tween 20 (T20) to yield a 2×TE+0.05% T20 buffer, (ii) Milli-Q water and Tween20 to yield a 1×TE+0.05% T20 buffer. The measuring buffer contains 100 mM KCl and 10 mM $KH_2PO_4$ at pH 7. The background electrolyte used for measurements consisted of 0.1 M KCl and 0.01 M $KH_2PO_4$ adjusted to pH 7 (phosphate buffer).

Photo-electrochemical measurements were carried out with PalmSens4 potentiostat (PalmSens, The Netherlands) using PSTrace software. Diode lasers operating at 655 nm, 532 nm and 405 nm were purchased from Roithner Lasertechnik (Austria) and Light emitting diodes operating in the similar wavelengths as lasers were purchased from Thorlabs, Inc. The light power was adjusted to 30 mW using a light power meter (Thorlabs, Inc.). The diameter of the light beam was adjusted to illuminate the working electrodes. The on/off switch for illumination was preprogrammed and controlled by a trigger with a relay. The measurements were conducted in light-chopped conditions (10 s or 30 s ON and 60 s OFF).

The photo-electrochemical measurements with magnetic particles accumulated on the surface of a gold-sputtered planar electrode (AUTR10, Dropsens) were executed by placing a neodymium magnet underneath. As an alternative, a carbon screen printed electrode (IS-C-SPE), was tested in the same manner. Before the measurements, particles were re-suspended in 10 μL of phosphate buffer and gently transferred into the measuring drop, where all the particles quickly precipitated at the working electrode due to a neodymium magnet below it. Photocurrents in this setup were measured at −0.15 V vs. the SPE pseudo reference electrode (100±5 mV vs. SCE).

Example 1. Influence of the Presence of Redox Reporter and Particle

Figure 2:
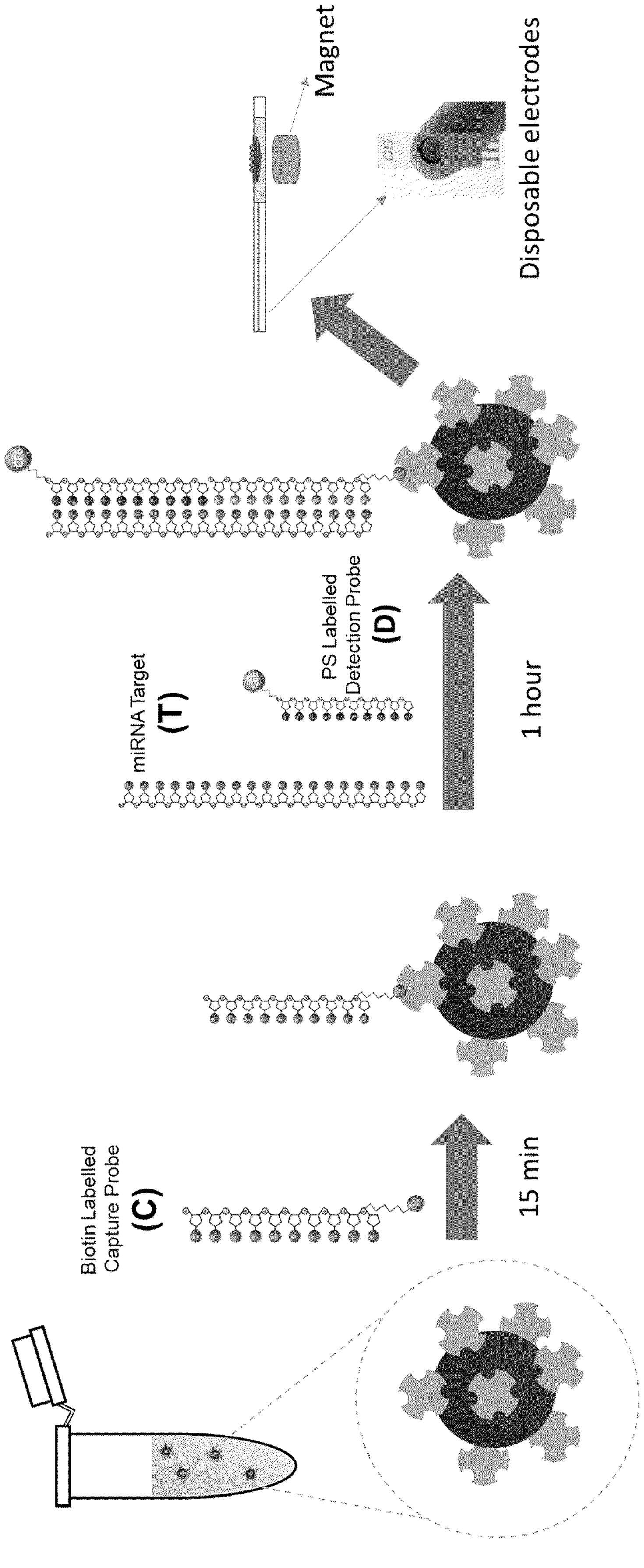
FIG. 2 represents a schematic view of the sample preparation method for the quantification of a nucleic acid sequence.

This first example is indicative for the quantification of the miRNA components, as schematically illustrated in FIG. 2. More specific, in this example, an example for the quantification of miR-141 is elaborated. Streptavidin-coated magnetic particles (10 μL, 10 mg/mL) were dispersed in an Eppendorf containing 1 mL 1×TE+0.05% T20 buffer. The solution was vortexed and the magnetic beads accumulated at the side of the Eppendorf directed to the magnetic rack (~1 min). The solution was removed and then 500 μL of double concentration capture probe (biotin labelled binding agent 1) solution, in our case 100 nM in Milli-Q+0.05% T20, was added to the beads leading to final incubation containing 1 mL of capture probe (binding agent 1) at 50 nM in 1×TE+0.05% T20. This lowers the NaCl concentration in the 2× buffer from 2 M to 1 M ensuring optimal binding of the capture probes. This solution was incubated for 10-15 min at room temperature using continuous rotation (10 rpm, rotary shaker). Following the incubation, the beads were accumulated again using a magnetic rack, and the solution was discarded and re-suspended in the detection probe (binding agent 2) solution (24 nM) and the target miR-141 (biological component) (20 nM) (for sandwich hybrid assay) with 1×TE+0.05% T20 and incubated for 1 hour at room temperature using gentle rotation (10 rpm, rotary shaker). For the duplex assay containing only two DNA strands, following the incubation with biding agent 1, the beads were accumulated again using a magnetic rack, and the solution was discarded and re-suspended in the detection probe (binding agent 2) complementary to miR-21 solution (20 nM). Following the incubation, the beads were washed 3 times with 1 mL 1×TE+0.05% T20 buffer and stored in 10 μL of the same buffer until measurements. After completion of the hybridization assay, a drop (10 μL) of the magnetic particle solution was introduced on the electrode and analyzed as indicated above. In this assay, the magnetic particles were attracted to the surface of the electrodes as indicated above.

A comparative analysis was made with a sandwich hybrid assay where the miRNA-141 strands were hybridized directly on the surface of the electrodes. Hereto, electrodes were incubated in 1 μM thiolated capture DNA probe (binding agent 1) containing 0.2 μM mercaptohexanol (MH, purity>98.0%, TCI chemicals) in 1×TE buffer (40 μL) overnight (~16 hours) and then in 1 mM MH for 2 h, for backfilling and removing weakly bound DNA molecules. For the hybridization step, a 40 μL drop consisting detection probe (binding agent 2) solution (24 nM) and the target miR-141 (biological component) (20 nM) was placed on the electrode for 1 h and washed with a copious amount of 1×TE+0.05% T20. After completion of the hybridization assay, the electrode with hybridized complex was subjected to photoelectrochemical measurements.

Figure 3:
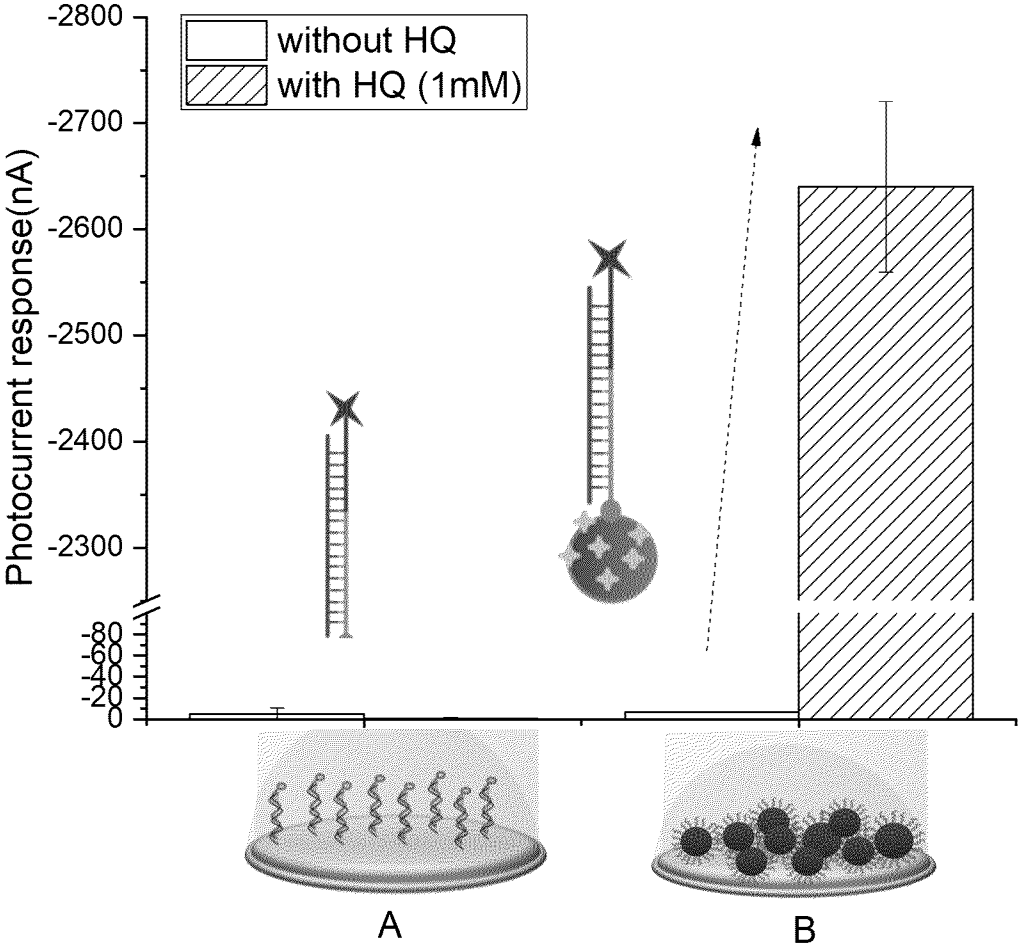
FIG. 3 shows the photocurrent signal generated by the method for the detection of miR-141 (20 nM), compared with the prior art method in the presence and absence of a redox reporter (hydroquinone). The experiment is executed with magnetic attraction of particles to the surface.

The results of the photo-electrochemical assay with the two different applied methodologies in combination with the absence/presence of a redox reporter (hydroquinone 1 mM) are shown in FIG. 3. This figure expresses clearly the positive effect of the introduction of the particles on the signal of the photo-electrochemical assay. Without the use of the particles, the response is much lower than the response when magnetic particles are introduced in the assay. It is assumed that, in the presence of the particles, an adequate distance is generated between the electrode surface and the place where the singlet oxygen is created. In this way, the redox reporter shuttle system is maintained in an efficient way. The presence of the redox reporter is indispensable since a comparative experiment without hydroquinone resulted in a photocurrent signal that is about 45 times lower.

Example 2. Quantitative Analysis of Different miR-Strands

To illustrate the performance of the elaborated method as a diagnostic tool, different concentrations of different miRNA-strands (miR-141, miR-145, miR-375) were analyzed as indicated above.

Figure 4:
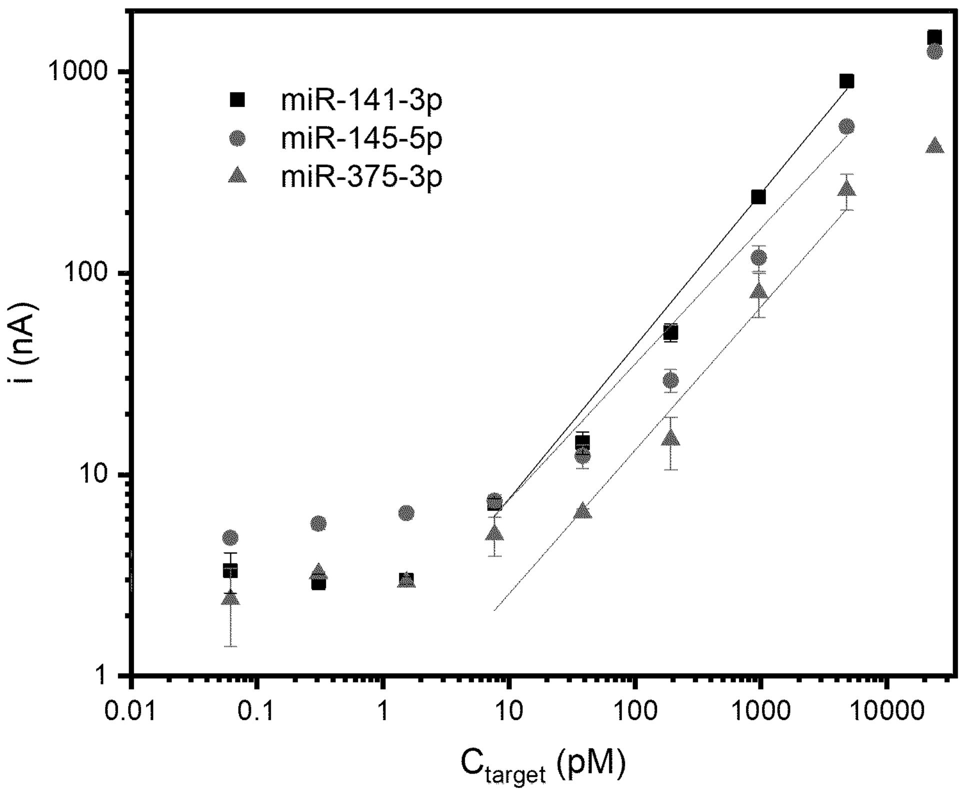
FIG. 4 shows the calibration curve for three different miR-strands (miR-141, miR-145, miR-375) with the method, involving magnetic attraction of the particles to the surface.

FIG. 4 shows the correlation between the concentrations and the generated photocurrent. The limit of detection for the different miRNA-strands are 4.6 pM (miR-141), 9.6 pM (miR-145) and 44.8 pM (miR-375). These numbers indicate the strength of the elaborated method as a diagnostic tool, also in a clinical setting.

Example 3. Effect of Attraction of the Particles to the Surface

To illustrate the effect of the attraction of the particles to the surface of the electrode, a comparative analysis was made, without and with the magnetic attraction of the magnetic particles as indicated above on the quantification of a concentration of 20 nM miR-141.

Figure 5:
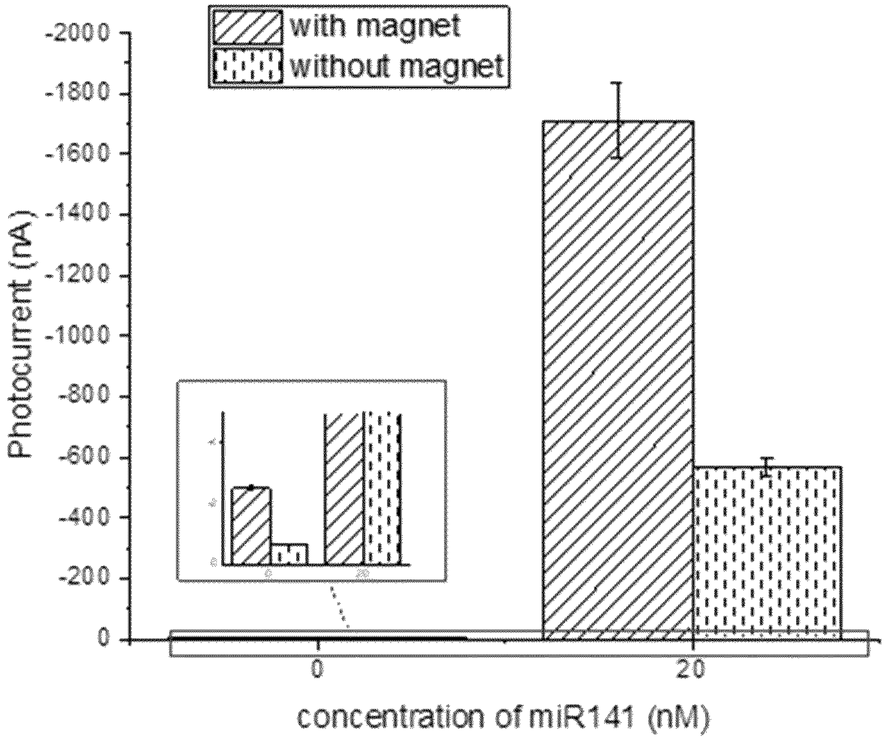
FIG. 5 shows the effect of the magnetic attraction of the particles to the surface electrode by the use of an external magnet. The photocurrent signal is generated for the detection of miR-141 in a concentration of 20 nM.

FIG. 5 shows the output of the photocurrent signal and although the signal with magnetic attraction is three times higher than without the magnetic attraction, the presence of this magnetic attraction seems not to be essential, especially for assays where low detection limits need not to be realized.

Example 4. Effect of the Electrode Surface

To illustrate the effect the type of electrode on the photocurrent signal, a comparative analysis was made with the execution of an identical assay on different electrode types: a gold thin film sputtered electrode (AUTR10) and a carbon screen printed electrode (IS-C-SPE). The electrodes were rinsed with ultrapure water without any additional pretreatment steps and the experiments were executed as indicated above. All electrode types were used for the quantification of a concentration of 24 nM miR-145.

Figure 6:
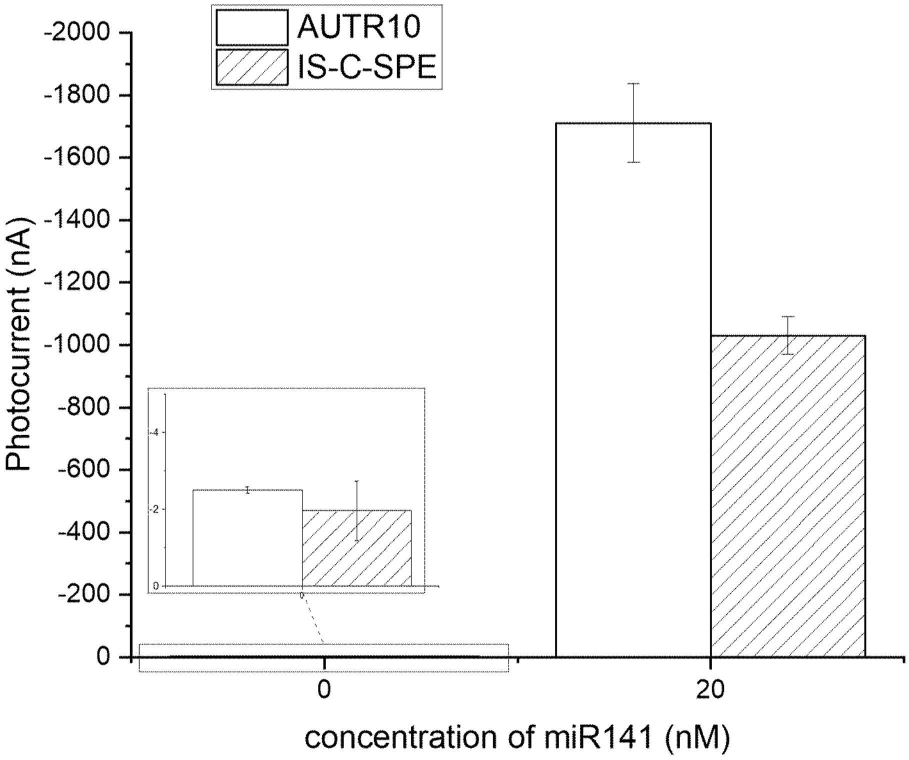
FIG. 6 shows the effect of the electrode type on the photocurrent signal for the detection of miR-141 (20 nM). The photocurrent signals, presented here are generated in combination with the magnetic attraction of the particles to the surface.

FIG. 6 shows the output of the photocurrent signal generated by the electrodes and the results indicate that higher signals were generated with the AUTR 10 electrode. Nevertheless, acceptable signals were retrieved with other electrodes, indicating that the method can be applied on a wide variety of electrode types.

Example 5. Execution of Multiplex Assays

To illustrate the possibility to perform a multiplex assay with the elaborated method, a DNA multiplex assay involving two types of binding agents 2 (methylene blue (MetB) and erythrosine b (Ery)) was executed in duplex assay format indicated above. Since MetB and are complementary regarding their activities in red and green light, it is possible to use them to detect two different complexes at once in a solution. As an initial proof of concept, complexes with two DNA sequences comprising of biotinylated binding agent 1 attached to magnetic particles and binding agent 2 complementary to miR-21. Four sets of components, two with MetB and other two with Ery were prepared independently as indicated above.

Figure 7:
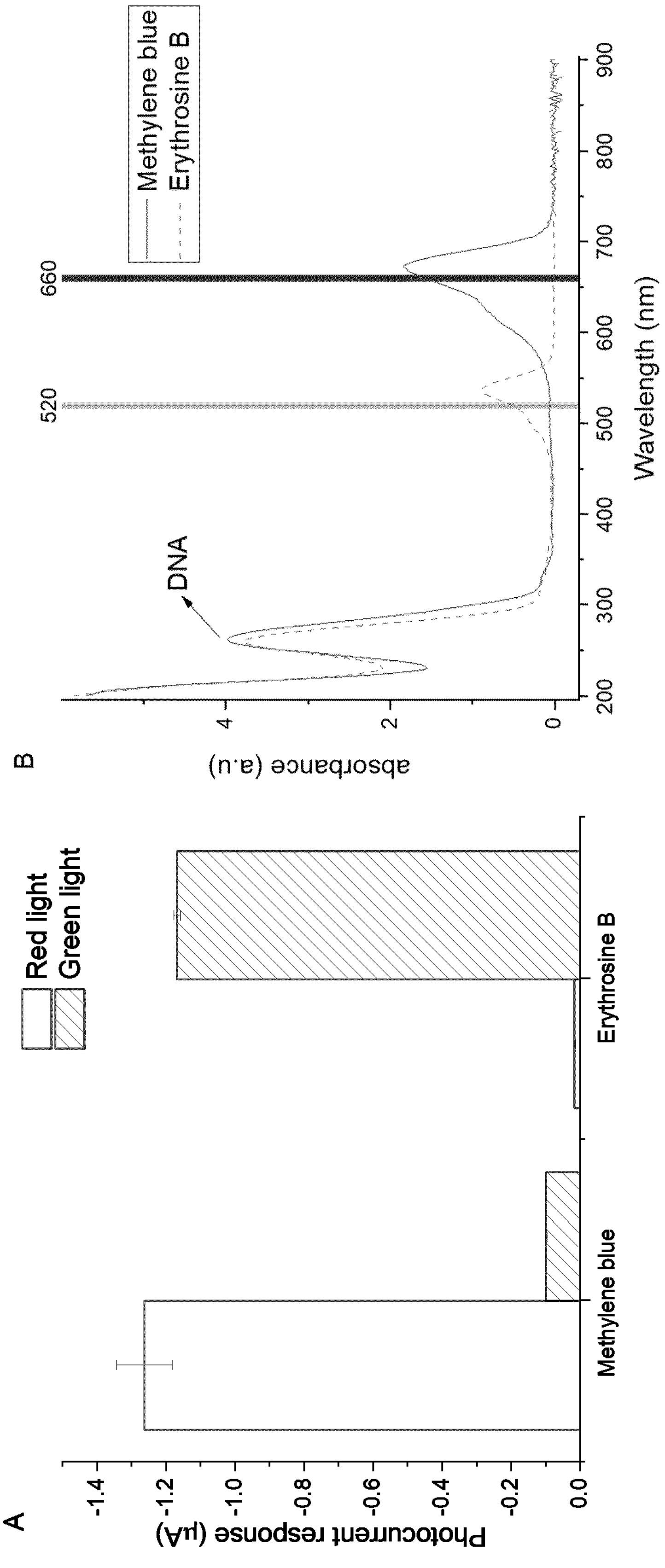
FIG. 7*a* shows the photocurrent signals for different labeled DNA sequences in a concentration of 20 nM. The two different type II photosensitizer labels are methylene blue and erythrosine b. As a light source, a red LED (working at 660 nm) and green LED (working at 520 nm) were used at an intensity of 30 mW.
FIG. 7*b* shows the UV-VIS absorption spectrum of 20 μM labeled DNA with the two type II photosensitizers in phosphate buffer.

FIG. 7 shows the output of the photocurrent signal as a result of the illumination of the sample with different LED-sources. It is observed that the complexes, labeled with methylene blue give a photocurrent signal only illuminated with red light but not with green light. The complexes, labeled with erythrosine b, only give a photocurrent signal with green light but not with red light. In this way, the proposed method shows its' ability to execute multiplex assays by labeling the specific components with a unique type II photosensitizer and to illuminate the sample with light that correspond with the unique type II photosensitizer.

Example 6. Effect of the Matrix

To illustrate the ability of the assay to detect biological components in clinically relevant samples an experiment was executed whereby miR spiked serum and plasma samples were analyzed as indicated as above. Before analysis, the serum and plasma samples were diluted in a 1:20 ratio with measuring buffer and the final concentration of the miR (miR-141) in the different samples was 10 pM.

Figure 8:
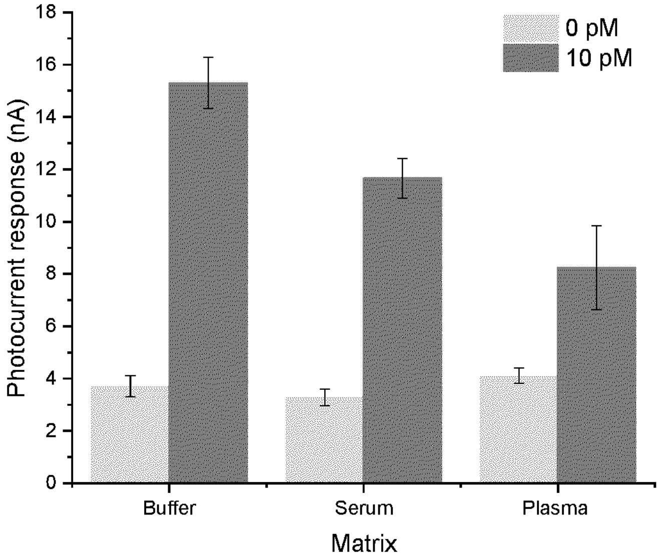
FIG. 8 shows the effect of the matrix on the photocurrent signals for the detection of miR-141 (10 pM). Measurements were executed at −0.2 V vs internal quasi reference, in a concentration of 1 mM hydroquinone in measuring buffer (pH7).

FIG. 8 shows the output of the photocurrent signals from the three matrices (pure buffer, serum and plasma). Although a decrease in output signal is observed for the spiked serum (with 24%) samples and for the spiked plasma (with 59%) samples compared with the spiked buffer samples, no significant difference is observed for the blank serum samples and the blank plasma samples compared to the blank buffer samples. These results indicate that no noticeable interaction occurs between the components present in serum and plasma and the components of the assay.

Example 7. DNA Point Mutation Detection Assay

To illustrate the ability of the assay to detect DNA point mutations, an assay was elaborated involving several point mutations of the KRAS gene, and more specifically of the KRAS G12C sequence. In order to obtain an optimal effective discrimination between the G12C sequence and wild type sequences, preliminary experiments were conducted to find the optimal temperature for the hybridization step. When the temperature is too low, the unspecific binding of the wild type sequences becomes too dominant. When the temperature is too high, the hybridization of the target sequence is blocked. This example is indicative for the quantification of DNA components by means of a sandwich assay.

Streptavidin-coated magnetic particles (10 μL, 10 mg/mL) were dispersed in an Eppendorf containing 1 mL 1×TE+0.05% T20. The solution was vortexed and the magnetic beads accumulated at the side of the Eppendorf directed to the magnetic rack (~1 min). The solution was removed and suspended in 500 μL of 2×TE+0.05% T20 buffer, then 500 μL of 100 nM capture probe in UltraPure-Water+0.05% T20, were added to the beads leading to a final incubation solution containing 1 mL of capture probe at 50 nM in 1×TE+0.05% T20. This lowers the NaCl concentration in the 2× buffer from 2 M to 1 M ensuring optimal binding of the capture probes. This concentration of capture probes was high enough to saturate all the beads with capture probes, given that the beads have a binding capacity of ~200 μmol of single-strand oligonucleotides per 1 mg of beads (according to the manufacturer's information sheet). This solution was incubated for 15 min at room temperature using continuous rotation (10 rpm, rotary shaker). Following the incubation, the beads were accumulated again using a magnetic rack, and the solution was discarded and the functionalized beads resuspended in 1×TE+0.05% T20 containing ChIE6 labeled detection probe (24 nM, concentration corresponding to the highest concentration of target used in this study), and target DNA, KRAS G12C, (24 nM) and incubated for 10 minutes at the selected temperature (67° C.) in an incubation oven at 10 rpm (rotary shaker). Following the incubation, the Eppendorfs were transferred to the magnetic rack, immersed in a water bath at the same temperature used in the incubation oven, to accumulate the beads. The beads were then washed 3 times with 1 mL 1×TE+0.05% T20, and stored in 10 μL 1×TE+0.05% T20 at room temperature until the PEC detection was performed.

PEC measurements were carried out using a PalmSens4 potentiostat (PalmSens, The Netherlands) using PSTrace 5.9 software. Gold sputtered planar electrode from DropSens AUTR 10 is the electrode used in all the PEC measurements unless stated otherwise.

The PEC measurements with magnetic particles accumulated on the surface of electrodes were executed by placing a neodymium magnet underneath. Before the measurements, particles were re-suspended in 10 μL of measuring buffer and gently transferred into the measuring drop (90 μL of measuring buffer placed on the SPE surface), where all the particles quickly precipitated at the working electrode due to a neodymium magnet underneath it.

Figure 9:
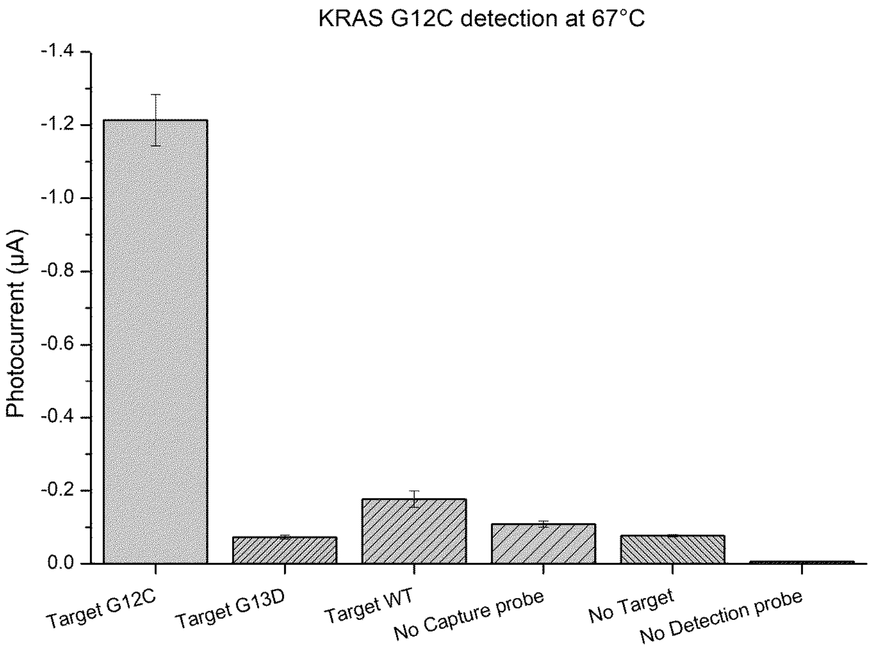
FIG. 9 shows the photocurrent signals for a DNA point mutation assay, involving the photocurrent signals of the assay with the target sequence (target KRAS G12C), of the assay involving a sequence with a mutation only four nucleotides away from the KRAS G12C (target G13D), of the assay involving a wild-type (WT) target differing from the target sequence by just one nucleotide. The figure includes in addition the results of the assays where no capture probe, target sequence, or detection probe were involved.

FIG. 9 shows clearly that the discrimination between the target sequence and the G13D sequence is maximal since comparable photocurrent signals were obtained with the negative controls whereas the discrimination efficiency with the wild type sequence is about 85%.

Analogueous experiments were conducted on the KRAS G13D and on the KRAS Q61H sequences. Similar results are observed as with the KRAS G12C sequences.

Example 8

To illustrate the effect of the use of multiple photosensitizers per binding agent, a miR assay (miR-145) was elaborated involving three photosensitizer (metB) molecules in the detection probe. A comparison was made with an assay involving only a single photosensitizer molecule in the detection probe. The miR sandwich hybrid assay was executed as indicated above with a concentration of 24 nM target molecule.

Figure 10:
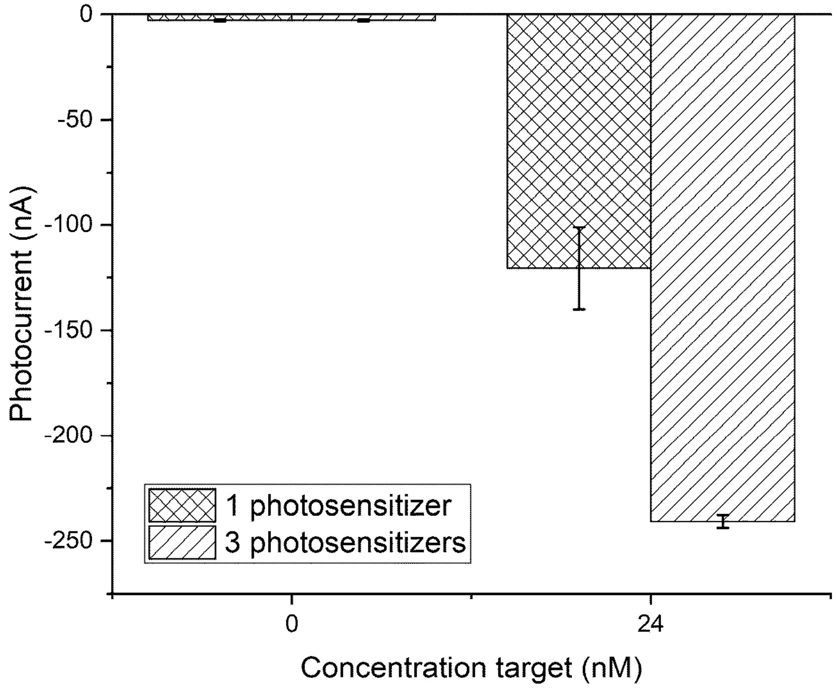
FIG. 10 shows the photocurrent signals of the miR assays (145, 24 nM) involving mutlipe (three) photosensitizer molecules versus a single photosensitizer molecule per detection probe.

FIG. 10 shows the output of the photocurrent signals for the different assays. The photocurrent signal of the assay with the three photosensitizer molecules is significantly higher than the signal of the assay with the single photosensitizer molecule.

REFERENCES

Trashin et al. (2017) Singlet oxygen-based electrosensing by molecular photosensitizers. Nature Communications 8:16108. DOI: 10.1038/ncomms 16108.

The invention claimed is:

1. A photo-electrochemical method for the detection and/or quantification of at least one biological component involving a. contacting a complex comprising i. a first binding agent labeled with a type II photosensitizer;

ii. a second binding agent linked to a particle;

wherein at least one of said first or said second binding agent is capable of binding to said biological component and, if one of said first or second binding agent is not capable of binding to said biological component, said binding agent is capable of binding to said other binding agent; wherein said binding of said first and/or second binding agent to said biological component and/or the binding of said binding agent to other binding agent do not interfere with each other; and wherein said binding of at least one of said binding agents to said biological component and/or of said other binding agent to said other binding agent is specific such that a complex is formed only with said biological component;

with an electrode comprising a surface;

b. illuminating said complex in the presence of a redox reporter; and c. detecting the photocurrent generated by the oxidation of said redox reporter at the surface of said electrode.

2. The method according to claim 1, wherein the particles are magnetic particles, and said particles are contacted to said electrode by magnetic attraction.

3. The method of claim 1, wherein the complex of step a is obtained by contacting a fluid sample comprising said biological component with (i) a first binding agent labeled with a type II photosensitizer capable of binding to said biological component and (ii) a second binding agent capable of binding to said biological component or to said first binding agent without interfering with the binding of said first binding agent to said biological component, said second binding agent being linked to a particle;

wherein said binding of said first binding agent to said biological component and/or said binding of said second binding agent to said first binding agent or to said biological component is specific such that a complex is formed only with said biological component.

4. The method of claim 1, which is a method of detecting two or more biological components, wherein said method comprises contacting two or more said complexes with an electrode, wherein the photosensitizer label of each of complex is sensitive to a different wavelength; wherein step b involves illuminating said complex with a wavelength corresponding to each of said photosensitizers and step c comprises detecting the photocurrent generated at each of said wavelengths.

5. The method of claim 1, wherein the biological component is an RNA or DNA sequence and said first and second binding agents are capable of hybridizing to said biological component.

6. The method of claim 1, wherein the biological component is a protein sequence and said first and second binding agents are capable of binding to said biological component.

7. The method of claim 1, wherein the redox reporter is selected from the list of hydroquinone, 4-aminophenol, 2 chlorophenol, bisphenol A or a 1:1 mixture of hydroquinone: L-ascorbic acid.

8. The method of claim 1, wherein the photosensitizer is selected from the list of chlorin e6, pheoporbide a, methyl pheophorbide, methylene blue, erythrosine, eosin, rosebengal.

9. The method of claim 1, wherein the first binding agent is labeled with two or more type II photosensitizers.

10. The method of claim 1, wherein said complex further comprises one or more additional binding agents labeled with a type II photosensitizer, wherein said one or more additional binding agents are capable of binding to said first or second binding agents and/or to each other, wherein said binding of said additional binding agents to said first or second binding or to each other does not interfere with the binding of said first and second binding agents to the biological component or to each other.

11. A photo-electrochemical system for the detection and/or quantification of at least one biological component involving a. an electrode b. a first binding agent labeled with a type II photosensitizer capable of binding to said biological component and c. a second binding agent capable of binding to said biological component or to said first binding agent without interfering with the binding of said first binding agent to said biological component, said second binding agent being linked to a particle wherein said binding of said first binding agent to said biological component and/or said binding of said second binding agent to said first binding agent or to said biological component is specific such that a complex is formed only with said biological component;

d. a redox reporter selected from the list hydroquinone, 4-aminophenol, 2 chlorophenol, bisphenol A or a 1:1 mixture of hydroquinone: L-ascorbic acid.

12. Kit for the execution of the photo-electrochemical method for the detection and/or quantification of at least one biological component comprising a. a first binding agent labeled with a type II photosensitizer capable of binding to said biological component and b. a second binding agent capable of binding to said biological component or to said first binding agent without interfering with the binding of said first binding agent to said biological component, said second binding agent being linked to a particle wherein said binding of said first binding agent to said biological component and/or said binding of said second binding agent to said first binding agent or to said biological component is specific such that a complex is formed only with said biological component;

c. a redox reporter selected from hydroquinone, 4-aminophenol, 2 chlorophenol, bisphenol A or a 1:1 mixture of hydroquinone: L-ascorbic acid.

13. The system of claim 11, wherein the first binding agent is labeled with two or more type II photosensitizers.

14. The system of claim 11, further comprising one or more additional binding agents labeled with a type II photosensitizer, wherein said one or more additional binding agents are capable of binding to said first or second binding agents and/or to each other, wherein said binding of said additional binding agents to said first or second binding or to each other does not interfere with the binding of said first and second binding agents to the biological component or to each other.

15. The kit of claim 12, wherein the first binding agent is labeled with two or more type II photosensitizers.

16. The kit of claim 12, further comprising one or more additional binding agents labeled with a type II photosensitizer, wherein said one or more additional binding agents are capable of binding to said first or second binding agents and/or to each other, wherein said binding of said additional binding agents to said first or second binding or to each other does not interfere with the binding of said first and second binding agents to the biological component or to each other.

17. The method of claim 1, wherein said complex is contacted with said electrode using a magnetic, electronic or gravitational force.

18. The method of claim 1, wherein said complex is contacted with said electrode using sedimentation or centrifugation.

* * * * *